(12) United States Patent
Masaki et al.

(10) Patent No.: US 7,794,084 B2
(45) Date of Patent: Sep. 14, 2010

(54) EYE FUNDUS CAMERA

(75) Inventors: Toshifumi Masaki, Tokyo (JP);
Toshiaki Okumura, Tokyo (JP); Shinya Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/566,051

(22) Filed: Sep. 24, 2009

(65) Prior Publication Data
US 2010/0085538 A1    Apr. 8, 2010

(30) Foreign Application Priority Data
Sep. 25, 2008    (JP) .............................. 2008-245860

(51) Int. Cl.
*A61B 3/14* (2006.01)
*A61B 3/12* (2006.01)
(52) U.S. Cl. ....................................... 351/206; 351/221
(58) Field of Classification Search ................. 351/206, 351/221, 205, 207, 208, 209, 210, 246
See application file for complete search history.

(56) References Cited
U.S. PATENT DOCUMENTS
7,306,336 B2 * 12/2007 Akita et al. ................. 351/206

7,445,337 B2 * 11/2008 Sekiguchi ................... 351/207

FOREIGN PATENT DOCUMENTS
JP    7-079926 A    3/1995
JP    2002-369802 A    12/2002

* cited by examiner

*Primary Examiner*—Hung X Dang
(74) *Attorney, Agent, or Firm*—Canon U.S.A., Inc., IP Division

(57) ABSTRACT

A single-plate image pickup element picks up an eye fundus image. A tricolor separation color filter includes R, G, and B filter elements arranged in a mosaic so as to correspond to the pixels of the image pickup element. Each virtual pixel value of color image data is calculated from light detection data of adjacent pixels. Thus, image data of a color still image is generated. The R filter elements transmit near-infrared light. Each virtual pixel value is calculated from light detection data of pixels corresponding to B or G filter elements that are adjacent to the R filters and have sensitivity to near-infrared light. Thus, image data of a near-infrared light monochrome moving image is generated.

4 Claims, 7 Drawing Sheets

EYE FUNDUS CAMERA

BACKGROUND OF THE INVENTION

1. Field of the Invention

The present invention relates to an eye fundus camera for observing and photographing the fundus of a subject's eye.

2. Description of the Related Art

Japanese Patent Laid-Open No. 7-79926 discloses a non-mydriatic eye fundus camera. During eye fundus observation using near-infrared light, for example, during alignment, the camera takes a moving image of an eye fundus using a dedicated monochrome camera having sensitivity to near-infrared light and displays the moving image, for example, on a monitor. When taking a still image using visible light, the camera takes a still color image using a general-purpose digital camera. Switching between optical paths is performed by a quick return mirror or a dichroic mirror.

Japanese Patent Laid-Open No. 2002-369802 discloses another non-mydriatic eye fundus camera, which uses a 3CCD camera. During eye fundus observation using near-infrared light, one of the three CCDs has sensitivity to near-infrared light. The camera generates a moving image of an eye fundus on the basis only of the output from the CCD having sensitivity to near-infrared light. When taking a still image using visible light, the camera generates a color still image on the basis of the RGB output from the three CCDs.

The eye fundus camera disclosed in Japanese Patent Laid-Open No. 7-79926 uses a dedicated monochrome camera and, for example, a quick return mirror. The eye fundus camera disclosed in Japanese Patent Laid-Open No. 2002-369802 does not need a dedicated monochrome camera, but the 3CCD camera uses a tricolor separation prism.

SUMMARY OF THE INVENTION

The present invention provides an eye fundus camera that performs near-infrared light monochrome moving image photographing using an image pickup unit for color still image photographing.

In an aspect of the present invention, an eye fundus camera includes an observation photographing optical system, an image pickup unit, a color filter for tricolor separation, and a calculation unit. The observation photographing optical system includes a near-infrared light generating unit that irradiates an eye fundus of a subject's eye with near-infrared light for near-infrared light observation, and a visible light generating unit that irradiates the eye fundus with light in the visible range for visible light photographing. The observation photographing optical system receives light reflected by the eye fundus and forms an eye fundus image. The image pickup unit picks up the eye fundus image formed by the observation photographing optical system and has a single-plate image pickup element. The color filter for tricolor separation includes R, G, and B filter elements arranged in a mosaic so as to correspond to pixels of the image pickup element. The calculation unit calculates each virtual pixel value of color image data from light detection data of adjacent pixels provided with the filter elements and generates image data of a color still image. At least one of the R, G, and B filter elements transmit near-infrared light. In the case of near-infrared light observation, the calculation unit calculates each virtual pixel value from light detection data of adjacent pixels provided with the filter elements that transmit near-infrared light and having sensitivity to near-infrared light, and generates image data of a near-infrared light monochrome moving image.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

The embodiments of the present invention will now be described in detail with reference to the drawings.

Figure 1:
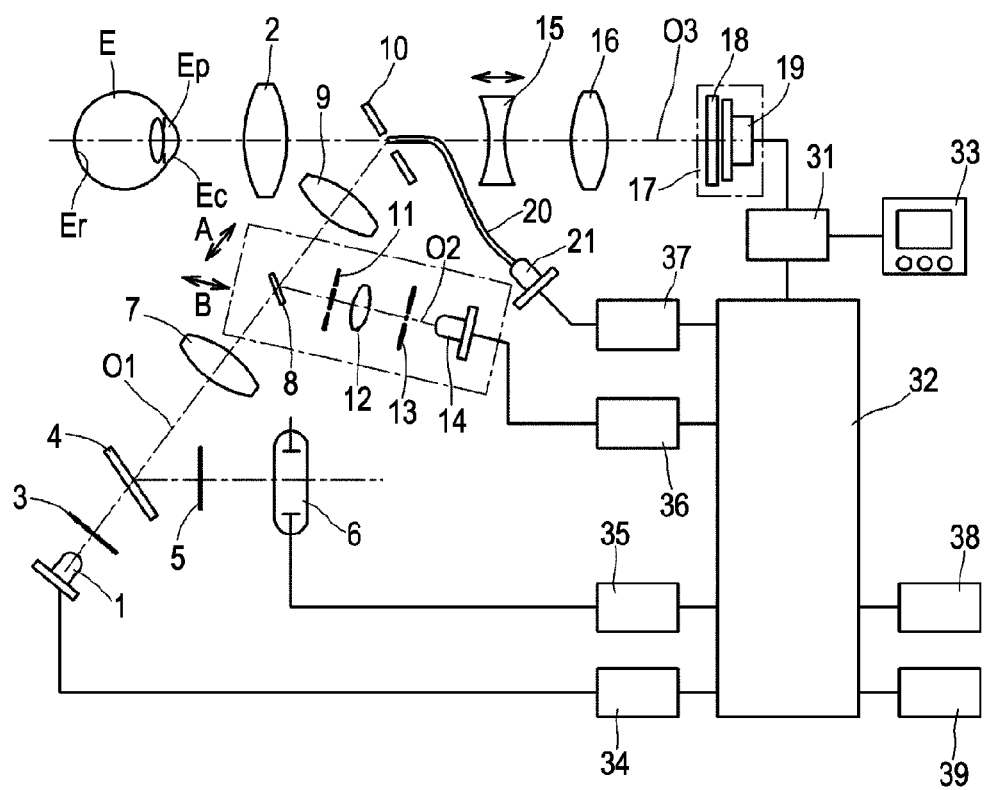
FIG. 1 is a configuration diagram of an eye fundus camera of an embodiment.

FIG. 1 is a configuration diagram of an eye fundus camera in a first embodiment. An observation light source 1 serves as a near-infrared light generating unit. In an optical path O1 leading from the observation light source 1 to an objective lens 2, a diaphragm 3 and a dichroic mirror 4 are disposed. The diaphragm 3 has a ring-like opening. In the incident direction of the dichroic mirror 4, a diaphragm 5 and a photographing light source 6 are disposed. The diaphragm 5 has a ring-like opening. The photographing light source 6 serves as a visible light generating unit. In the exiting direction of the dichroic mirror 4, a relay lens 7, a mirror 8, a relay lens 9, and an apertured mirror 10 are arranged in this order and make up an eye fundus illumination optical system.

In an optical path O2 in the incident direction on the mirror 8, a two-opening diaphragm 11, a lens 12, a focusing index 13, and a focusing index light source 14 are disposed and make up a focusing index projection optical system.

In an optical path O3 in the transmission direction of the apertured mirror 10, a focusing lens 15, a photographing lens 16, and an image pickup unit 17 are arranged and make up an observation photographing optical system. In the image pickup unit 17, a tricolor separation color filter 18 and a single-plate image pickup element 19 are provided. The aperture of the apertured mirror 10 is connected by an optical fiber 20 to an alignment index light source 21.

The focusing index projection optical system moves in conjunction with the focusing lens 15 in the direction A and projects the focusing index 13 onto the eye fundus Er of a subject's eye E. During still image photographing, the focusing index projection optical system moves in the direction B and is retracted from the illumination optical system.

The output of the image pickup unit 17 is connected through an image signal processing unit 31 to a calculation control unit 32 and a display 33 capable of displaying a VGA resolution image. The output of the calculation control unit 32 is connected to the observation light source 1 through an observation light source drive circuit 34, and to the photographing light source 6 through a photographing light source drive circuit 35. The output of the calculation control unit 32 is also connected to the focusing index light source 14 through a focusing index light source drive circuit 36, and to the alignment index light source 21 through an alignment index light source drive circuit 37. In addition, the calculation control unit 32 is connected to an input portion 38 and a recording portion 39.

During eye fundus observation, the calculation control unit 32 drives the observation light source drive circuit 34 and turns on and modulates the observation light source 1. Light rays emitted from the observation light source 1 pass through the diaphragm 3 and the dichroic mirror 4. The observation light source 1 is a near-infrared LED having a center wavelength of 850 nm. The dichroic mirror 4 transmits infrared light and reflects visible light. Therefore, light rays emitted from the observation light source 1 pass through the dichroic mirror 4. Light rays passing through the dichroic mirror 4 pass through the relay lens 7, the mirror 8, and the relay lens 9, are reflected by the apertured mirror 10, pass through the objective lens 2, the cornea Ec of the subject's eye E, and the pupil Ep, and illuminate the eye fundus Er.

The calculation control unit 32 drives the focusing index light source drive circuit 36 and turns on the focusing index light source 14. The focusing index light source 14 is a near-infrared LED having a center wavelength of 850 nm. Light rays from the focusing index light source 14 illuminate the focusing index 13. The image of the focusing index 13 passes through the lens 12, is reflected by the mirror 8, is superposed on the light rays from the observation light source 1, and is projected onto the eye fundus Er of the subject's eye E.

The illuminated eye fundus image and index image pass through the pupil Ep of the subject's eye E, the cornea Ec, the objective lens 2, the aperture of the apertured mirror 10, the focusing lens 15, the photographing lens 16, and the tricolor separation color filter 18 in the image pickup unit 17, and are focused onto the image pickup element 19.

At the same time, the calculation control unit 32 drives the alignment index light source drive circuit 37 and turns on the alignment index light source 21. The alignment index light source 21 is a near-infrared LED having a center wavelength of 850 nm. Light rays from the alignment index light source 21 pass through the optical fiber 20 and the objective lens 2. The cornea Ec of the subject's eye E is irradiated with the light rays. Light reflected by the cornea Ec is superposed on light emitted from the observation light source 1 and reflected by the eye fundus Er and light emitted from the focusing index light source 14 and reflected by the eye fundus Er, and is focused onto the image pickup element 19.

The image pickup element 19 converts the focused eye fundus image, focusing index image, and alignment index images into electric signals. The image signal processing unit 31 reads out data from the image pickup element 19 and amplifies the data. Digital moving image data is generated, and a moving image is displayed on the display 33.

Figure 2A:
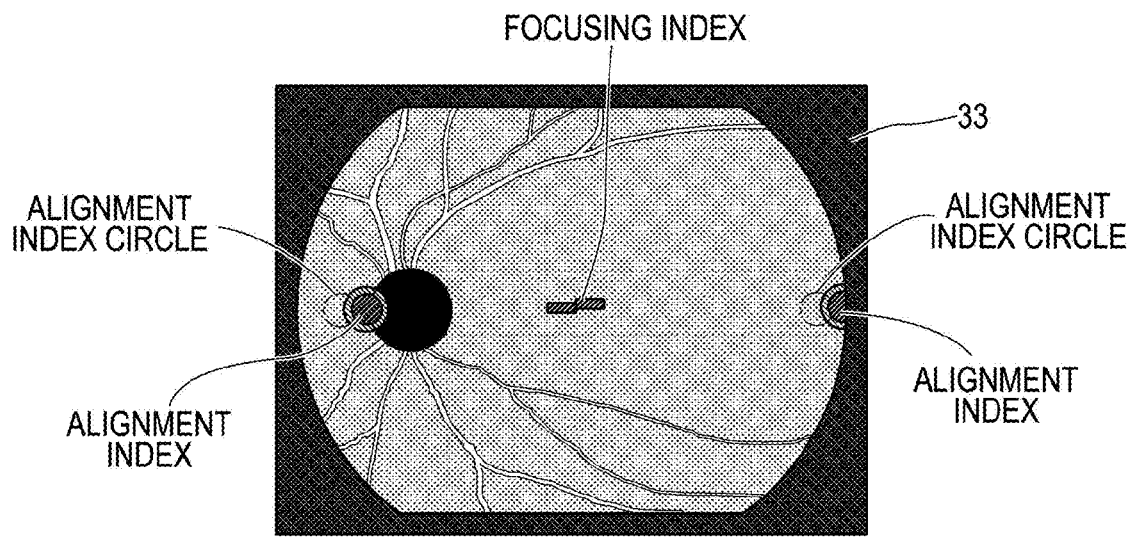
FIGS. 2A and 2B are illustrations of alignment and focusing.
Figure 2B:
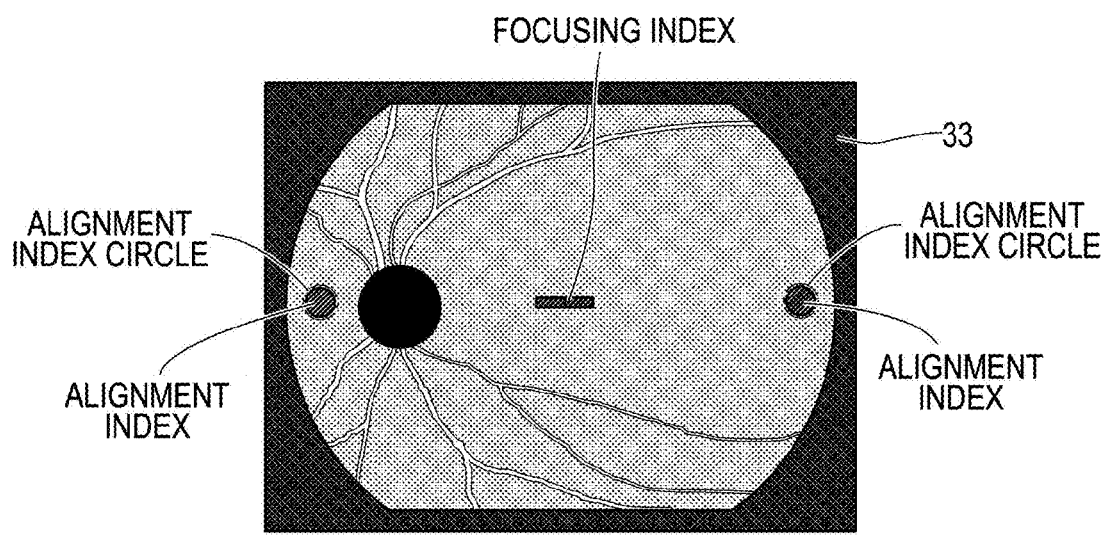

FIGS. 2A and 2B are illustrations of alignment and focusing. The observation light source 1, the focusing index light source 14, and the alignment index light source 21 each have a center wavelength in the near-infrared region and operate in a non-mydriatic mode. FIG. 2A shows an unaligned and unfocused state. An operator aligns and focuses the fundus image of the subject's eye E using near-infrared light while viewing the focusing index and the alignment indexes in this image.

When the alignment and focusing are completed, the right and left bars of the focusing index image are aligned and each alignment index is located in its corresponding alignment index circle as shown in FIG. 2B.

Figure 3:
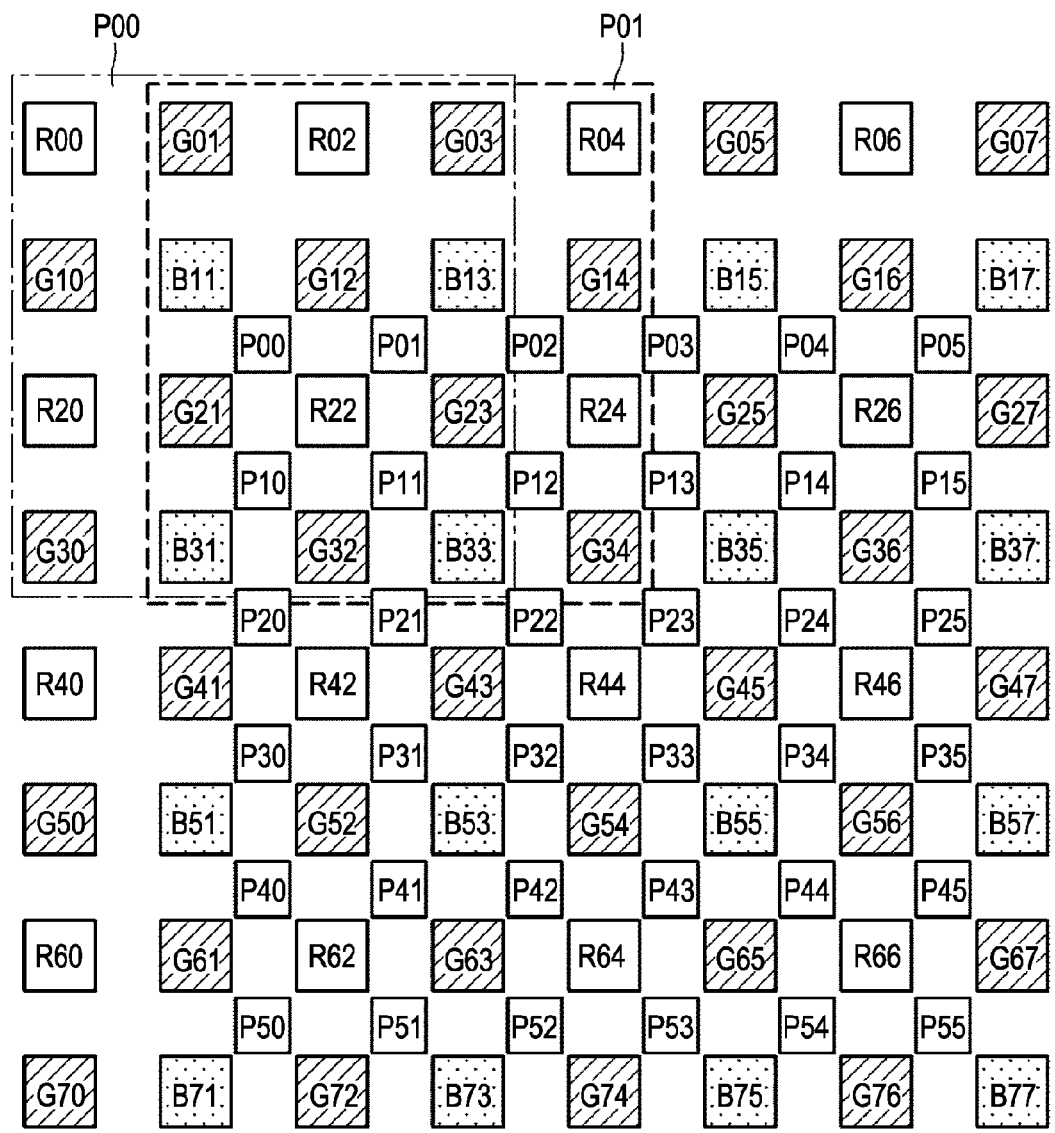
FIG. 3 shows the arrangement of filter elements of a tricolor separation color filter and virtual pixels in the case of color still image photographing.
Figure 4:
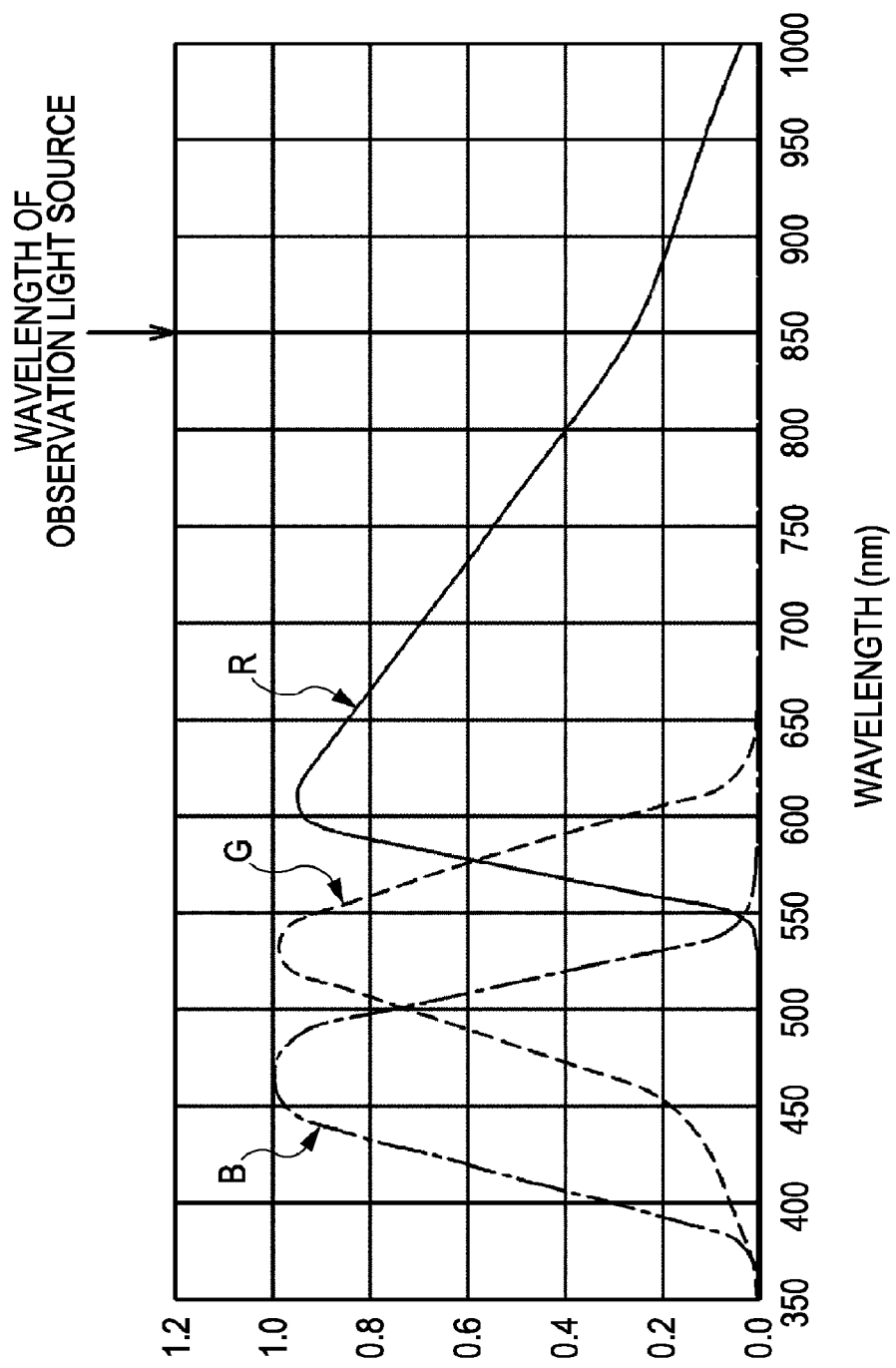
FIG. 4 shows the spectral sensitivity characteristic of an image pickup unit in which only the pixels provided with an R filter element have sensitivity to near-infrared light.

The tricolor separation filter 18, which is disposed in front of the image pickup element 19 in the image pickup unit 17, includes red (R), green (G), and blue (B) filter elements arranged in a mosaic so as to correspond to each pixel of the image pickup element 19 as shown in FIG. 3. The spectral sensitivity characteristic of the image pickup unit 17, which is a combination of the color filter 18 and the image pickup element 19, is as shown in FIG. 4.

The image signal processing unit 31 reads out data of each pixel from the image pickup element 19, amplifies the data, calculates the virtual pixel values according to the mode of the eye fundus camera, and generates image data of a color still image or a near-infrared monochrome moving image.

The calculation of each virtual pixel value during the generation of an image will be described. In the case of color still image photographing, the virtual pixel value P00 shown in FIG. 3 is calculated by a color dither method.

The value of each of colors R, G, and B of the virtual pixel P00 is calculated using light detection data of pixels R00, R02, B11, G12, B13, R20, G21, R22, B31, and B33 out of the pixels surrounded by alternate long and short dash line. When the values of R, G, and B of the virtual pixel P00 are denoted as P00*r*, P00*g*, and P00*b*, respectively, P00*r*, P00*g*, and P00*b* are calculated as follows:

$$P00g=(G12+G21)/2$$

$$P00r=(9\cdot R22+3\cdot R02+3\cdot R20+R00)/16$$

$$P00b=(9\cdot B11+3\cdot B13+3\cdot B31+B33)/16$$

The value of each of colors R, G, and B of the right neighboring virtual pixel P01 is calculated from the light detection data of pixels R02, R04, B11, G12, B13, R22, G23, R24, B31, and B33 out of the pixels surrounded by dashed line. When the values of R, G, and B of the virtual pixel P01 are denoted as P01*r*, P01*g*, and P01*b*, respectively, P01*r*, P01*g*, and P01*b* are calculated as follows:

$$P01g=(G12+G23)/2$$

$$P01r=(9\cdot R22+3\cdot R02+3\cdot R24+R04)/16$$

$$P01b=(9\cdot B13+3\cdot B11+3\cdot B33+B31)/16$$

In a similar manner, virtual pixel values are calculated from the light detection data in the range of 4×4 adjacent pixels in each virtual pixel P. Thus, the data of a color image is generated.

When the image pickup element 19 has about 5,000,000 pixels, and when the resolution required for a moving image is VGA (640×480), about 300,000 pixels are required, and the number of pixels of a near-infrared monochrome moving image is 1/16 of that of a color still image.

Figure 5:
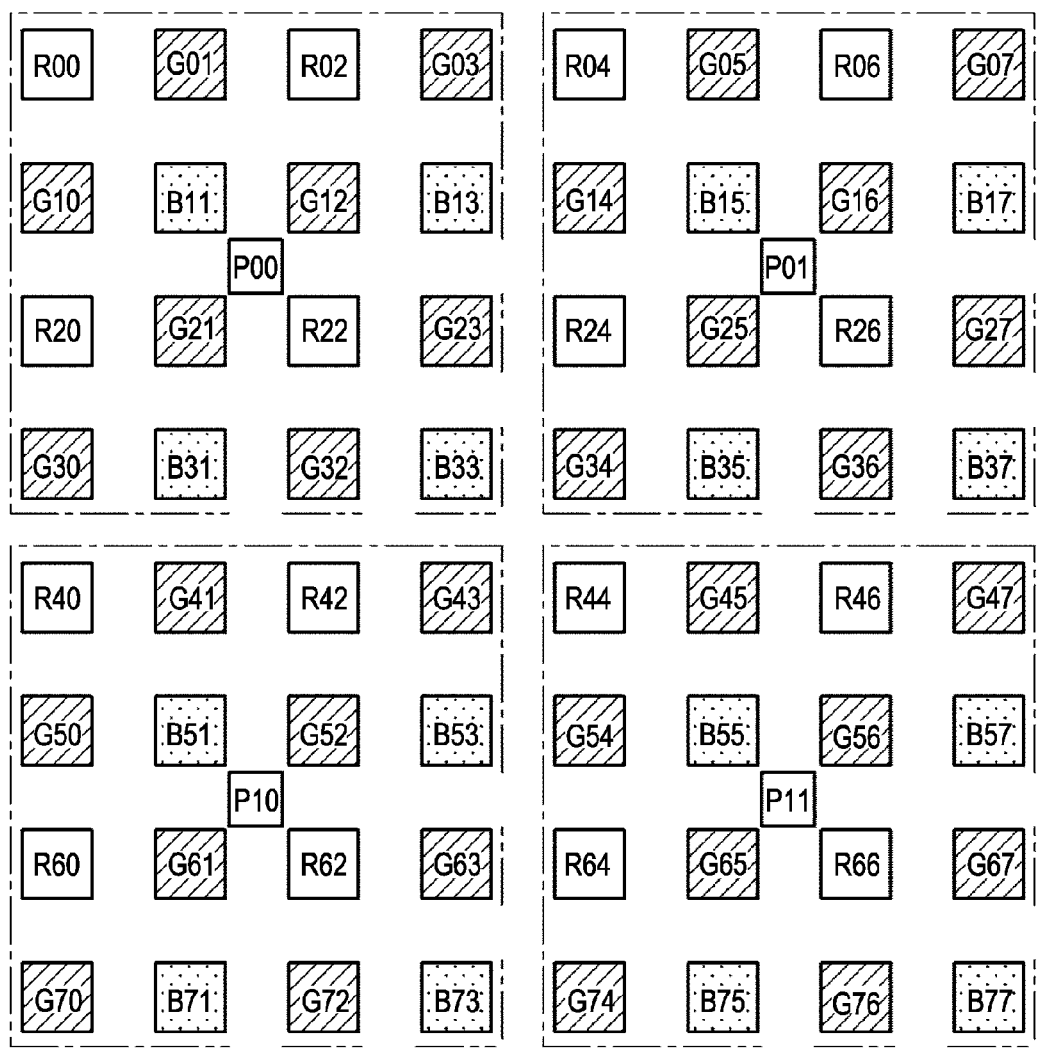
FIG. 5 shows the arrangement of filter elements of a tricolor separation color filter and virtual pixels in the case of near-infrared light monochrome moving image photographing.

In this case, virtual pixels are arranged as shown in FIG. 5, at intervals of three virtual pixels of a still image in both the vertical and horizontal directions so that the number of pixels of a moving image is 1/16 of that of a still image.

When the image pickup unit 17 has the spectral sensitivity characteristic of FIG. 4, only the pixels provided with R filter have sensitivity to near-infrared light of the observation light source 1. In this case, the value of a virtual pixel is denoted as P00$ir$, and weighting is performed according to the positional relationship of adjacent pixels. P00$ir$ is calculated as follows:

$$P00ir=(9·R22+3·R02+3·R20+R00)/16$$

$$P00ir=(9·R26+3·R06+3·R24+R04)/16$$

The light detection data of each pixel may be weighted using other variable factors.

With respect to R, G, and B, the same data is output, and a monochrome image is thereby output. If the sensitivity to near-infrared light is insufficient, data may be simply added as follows:

$$P00ir=R00+R02+R20+R22$$

$$P00ir=R04+R06+R24+R26$$

Figure 6:
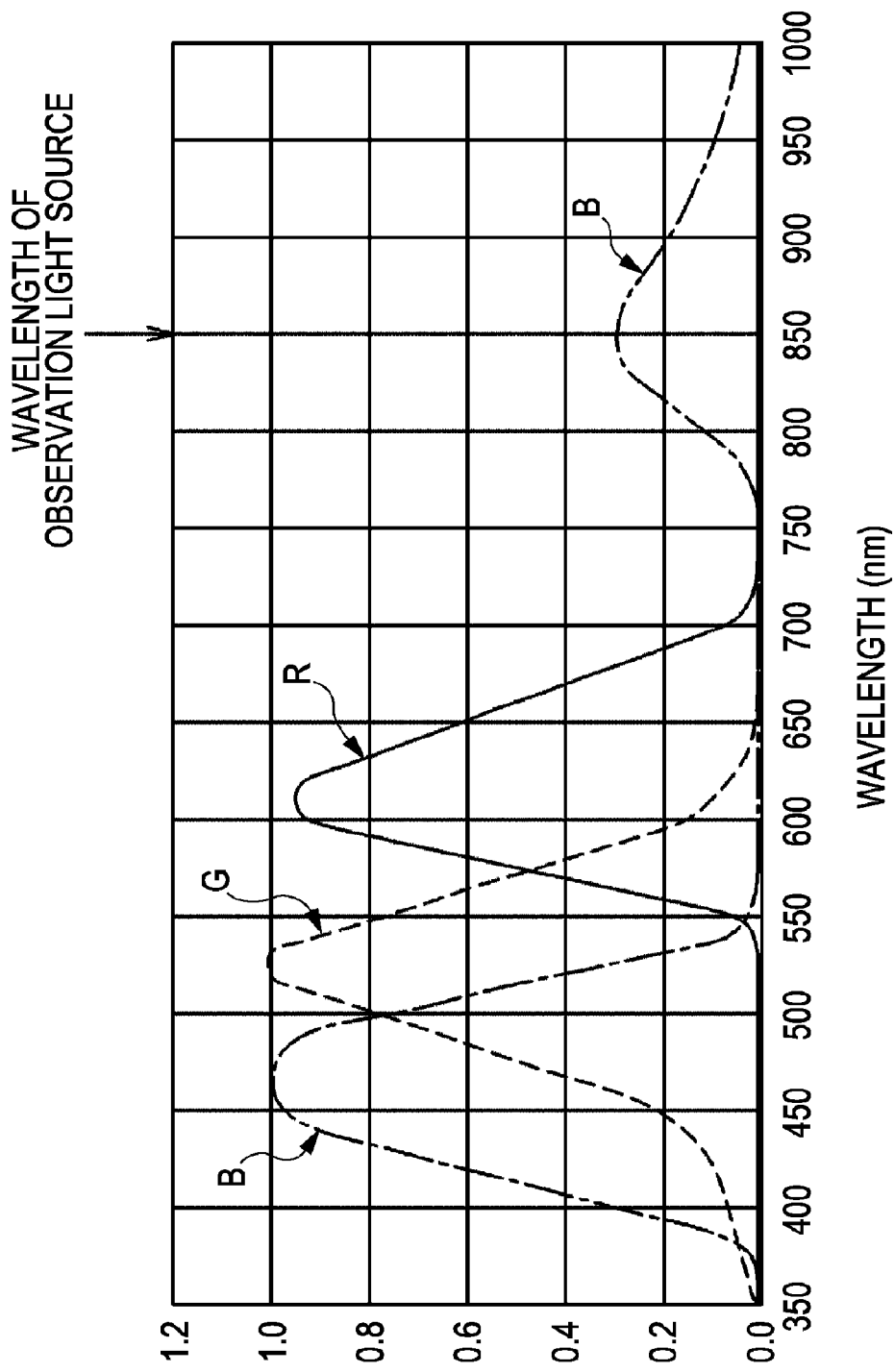
FIG. 6 shows the spectral sensitivity characteristic of an image pickup unit in which only the pixels provided with a B filter element have sensitivity to near-infrared light.

When, in the color filter 18 shown in FIG. 3, B filter elements transmit near-infrared light and the number of B filter elements is larger than those of R and G filter elements, the spectral sensitivity characteristic of the image pickup unit 17 is as shown in FIG. 6. Only the pixels provided with a B filter element have sensitivity to near-infrared light of the observation light source 1. In this case, the value of a virtual pixel of near-infrared light is denoted as P00$ir$, and weighting is performed in a similar manner. P00$ir$ is calculated as follows:

$$P00ir=(9·B11+3·B13+3B31+B33)/16$$

$$P00ir=(9·B13+3·B11+3·B33+B31)/16$$

With respect to R, G, and B, the same data is output, and a monochrome image is thereby output. If the sensitivity to near-infrared light is insufficient, data may be simply added as follows:

$$P00ir=B11+B13+B31+B33$$

$$P01ir=B13+B11+B33+B31$$

Figure 7:
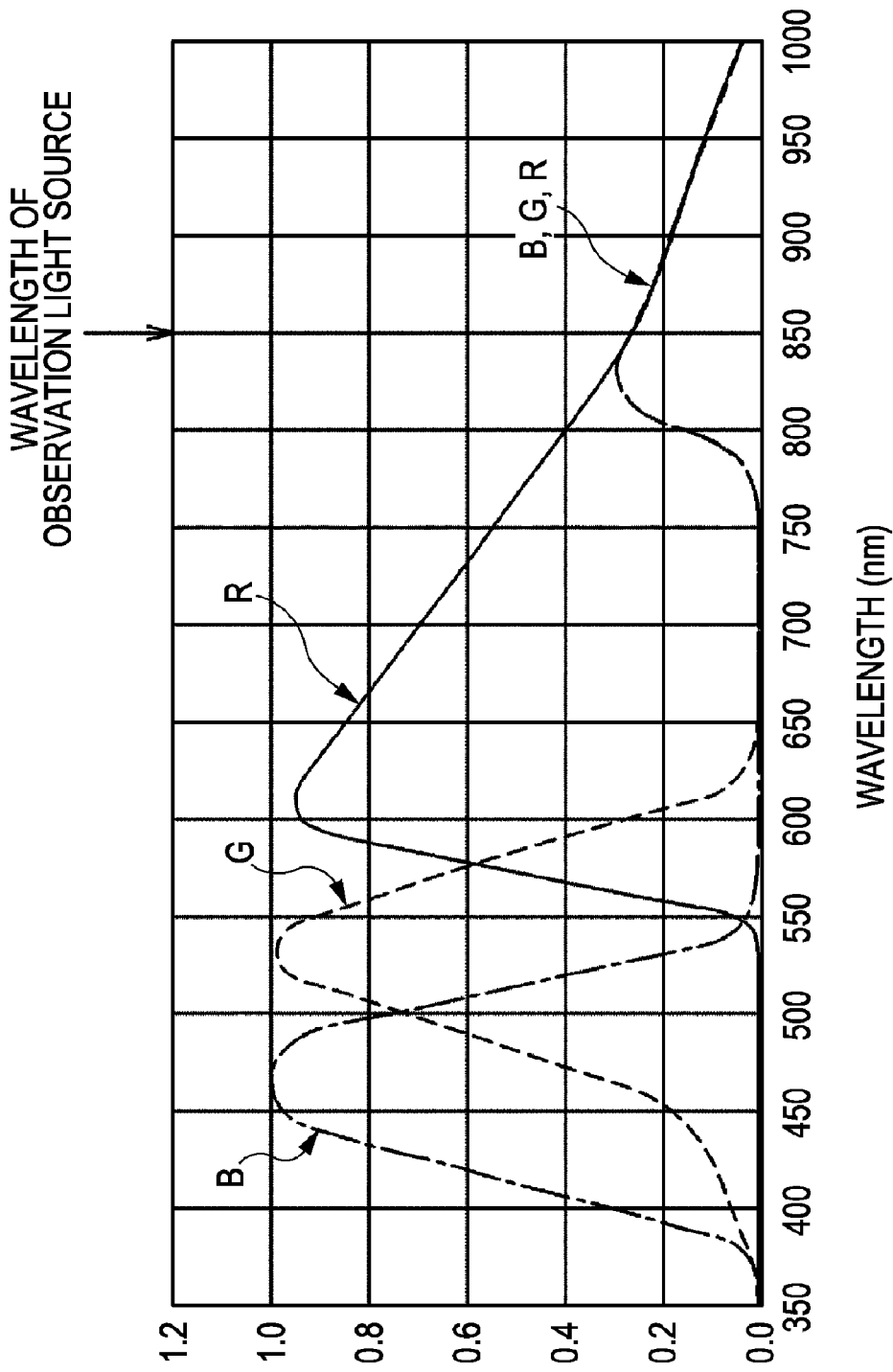
FIG. 7 shows the spectral sensitivity characteristic of an image pickup unit in which the pixels provided with an R filter element, the pixels provided with a G filter element, and the pixels provided with a B filter element all have sensitivity to near-infrared light.

When the ratio of the numbers of R, B, and G filter elements in the color filter 18 is changed and the image pickup unit 17 has a spectral sensitivity characteristic in which R, G, and B pixels each have sensitivity to near-infrared light of the observation light source 1 as shown FIG. 7, P00$ir$ is calculated as follows:

$$P00ir=R00+G01+R02+G03+G10+B11+G12+B13+\\R20+G21+R22+G23+G30+B31+G32+B33$$

$$P00ir=R04+G05+R06+G07+G14+B15+G16+B17+\\R24+G25+R26+G27+G34+B35+G36+B37$$

As described above, in this embodiment, a color still image is generated during eye fundus photographing. During eye fundus observation, image data of a near-infrared light monochrome moving image having a resolution lower than that of a color still image is generated, and a monochrome image of an eye fundus can be observed.

To photograph an eye fundus, an operator presses a photographing switch in the input portion 38 when the image on the display 33 is aligned and focused as shown in FIG. 2B. The calculation control unit 32 detects this and drives the photographing light source drive circuit 35 to turn on the photographing light source 6. The image signal processing unit 31 is changed to the color still image photographing mode by the calculation control unit 32.

At the same time, the calculation control unit 32 drives the alignment index light source drive circuit 37 to turn off the alignment index light source 21, and drives the focusing index projection optical system in the direction B out of the optical path O1.

Light rays in the visible light range emitted from the photographing light source 6 pass through the diaphragm 5, are reflected by the dichroic mirror 4, which reflects visible light, follow the same path as the light rays from the observation light source 1, and illuminate the eye fundus Er of the subject's eye E. The light reflected by the eye fundus Er passes through the tricolor separation color filter 18 and forms an image of the eye fundus Er on the image pickup element 19.

The image pickup element 19 performs photoelectric conversion. The resulting electric signal is read out by the image signal processing unit 31. The image signal processing unit 31 calculates each virtual pixel value for a color still image as described above to generate data of a color still image. The data is recorded in the recording portion 39 through the calculation control unit 32. The data can be displayed on the display 33 by reducing the resolution of the data.

As described above, the eye fundus camera according to the present invention performs near-infrared light monochrome moving image photographing using an image pickup unit for color still image photographing.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2008-245860 filed Sep. 25, 2008, which is hereby incorporated by reference herein in its entirety.

What is claimed is:

1. An eye fundus camera comprising:
    an observation photographing optical system including a near-infrared light generating unit that irradiates an eye fundus of a subject's eye with near-infrared light for near-infrared light observation, and a visible light generating unit that irradiates the eye fundus with light in the visible range for visible light photographing, the observation photographing optical system receiving light reflected by the eye fundus and forming an eye fundus image;
    an image pickup unit that picks up the eye fundus image formed by the observation photographing optical system and has a single-plate image pickup element;
    a color filter for tricolor separation including R, G, and B filter elements arranged in a mosaic so as to correspond to pixels of the image pickup element; and
    a calculation unit that calculates each virtual pixel value of color image data from light detection data of adjacent pixels provided with filter elements and generates image data of a color still image,
    wherein at least one of the R, G, and B filter elements transmit near-infrared light, and in a case of near-infrared light observation, the calculation unit calculates each virtual pixel value from light detection data of adjacent pixels provided with the filter elements that transmit near-infrared light and having sensitivity to near-infrared light, and generates image data of a near-infrared light monochrome moving image.

2. The eye fundus camera according to claim 1, wherein when the image data of a near-infrared light monochrome moving image is generated, each virtual pixel value is calculated by adding light detection data of adjacent pixels having sensitivity to near-infrared light.

3. The eye fundus camera according to claim 1, wherein when the image data of a near-infrared light monochrome moving image is generated, each virtual pixel value is calculated by performing weighting according to the positional relationship of adjacent pixels having sensitivity to near-infrared light.

4. The eye fundus camera according to claim 3, wherein factors of the weighting are variable.

* * * * *